United States Patent [19]
Zirps et al.

[11] Patent Number: 5,899,914
[45] Date of Patent: May 4, 1999

[54] SURGICAL INSTRUMENT

[75] Inventors: Christopher T. Zirps, Milton; William R. Rebh, Shrewsbury, both of Mass.

[73] Assignee: Endius Incorporated, Plainville, Mass.

[21] Appl. No.: 08/872,831

[22] Filed: Jun. 11, 1997

[51] Int. Cl.⁶ .................................................. A61B 17/32
[52] U.S. Cl. ..................... 606/170; 606/205; 606/206; 606/174
[58] Field of Search .................... 606/170, 174, 606/205, 206, 207, 208

[56] References Cited

U.S. PATENT DOCUMENTS

| | | |
|---|---|---|
| 3,470,876 | 10/1969 | Barchilon . |
| 3,605,725 | 9/1971 | Bentov . |
| 4,662,371 | 5/1987 | Whipple et al. ......................... 606/174 |
| 5,300,087 | 4/1994 | Knoeplfler ............................... 606/207 |
| 5,507,773 | 4/1996 | Huitema et al. ......................... 606/207 |
| 5,618,294 | 7/1995 | Aust et al. ............................... 606/174 |
| 5,649,955 | 3/1995 | Hashimoto et al. ..................... 606/170 |

FOREIGN PATENT DOCUMENTS

| | | |
|---|---|---|
| 0301288A1 | 2/1989 | European Pat. Off. . |
| 2662778 | 12/1991 | France . |
| 3920706A1 | 1/1991 | Germany . |
| 4136861A1 | 5/1993 | Germany . |
| 4204051A1 | 8/1993 | Germany . |
| 9300048 | 1/1993 | WIPO . |
| 9304634 | 3/1993 | WIPO . |
| 9320760 | 10/1993 | WIPO . |

*Primary Examiner*—Michael Buiz
*Assistant Examiner*—Daphna Shai
*Attorney, Agent, or Firm*—Tarolli, Sundheim, Covell, Tummino & Szabo

[57] ABSTRACT

A surgical instrument (10) includes a handle (12), a rigid stem section (20) extending from the handle, and a flexible stem section (24) extending from the rigid stem section. A surgical tool (30) connected with a distal end of the flexible stem section (24) includes a fixed part (32) fixed for movement with the distal end of the flexible stem section (24) and a movable part (34) supported on the fixed part for pivotal movement. The instrument (10) includes a flexible actuator cable (180) having a first end portion (184) movable by an actuator member on the handle, an intermediate portion extending through the flexible stem section, and a second end portion (182) extending through a passage (248) in the movable part (34) and soldered in the passage. The flexible actuator cable (180) transmits force from the actuator member to the movable part (34) to effect pivotal movement of the movable part.

13 Claims, 5 Drawing Sheets

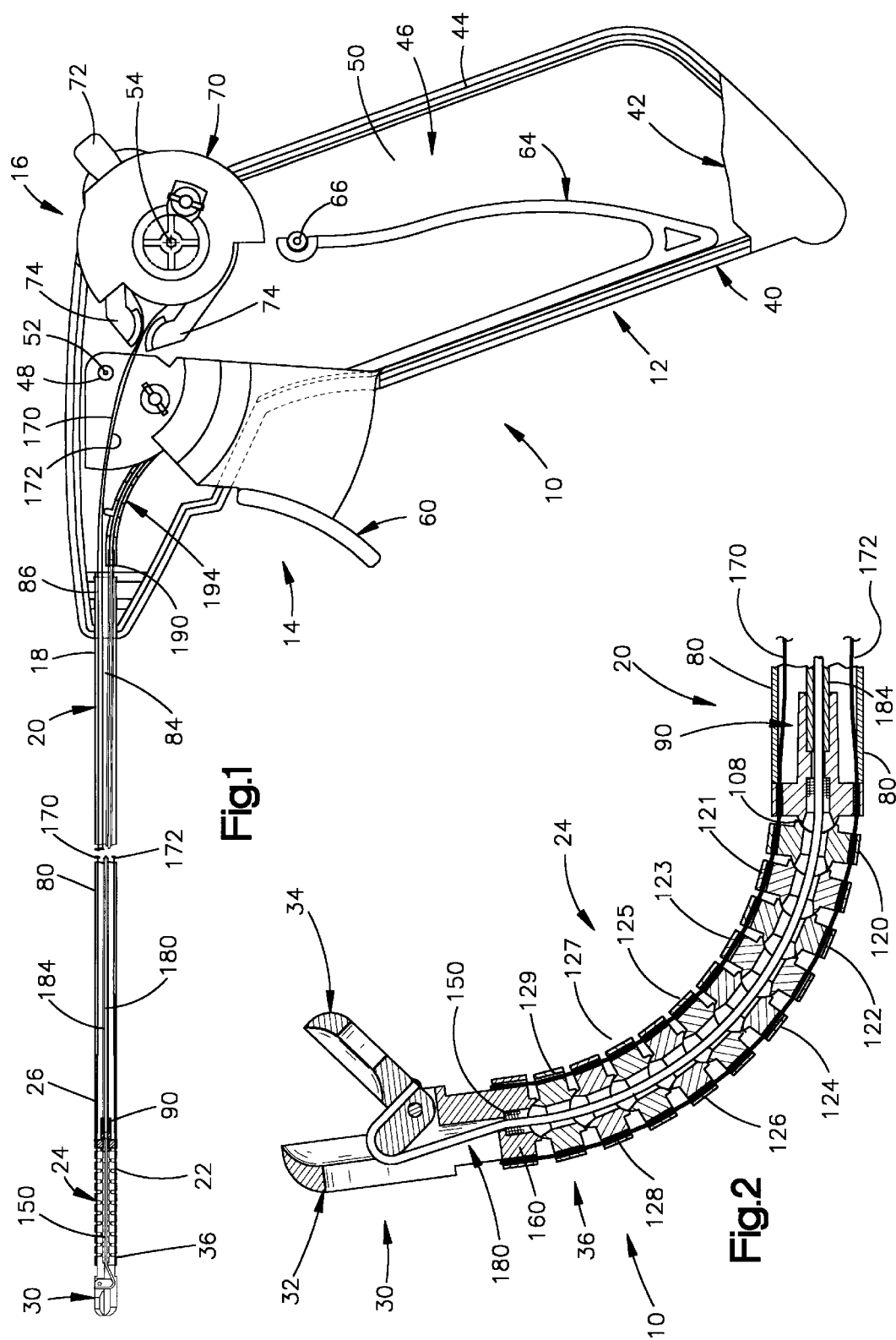

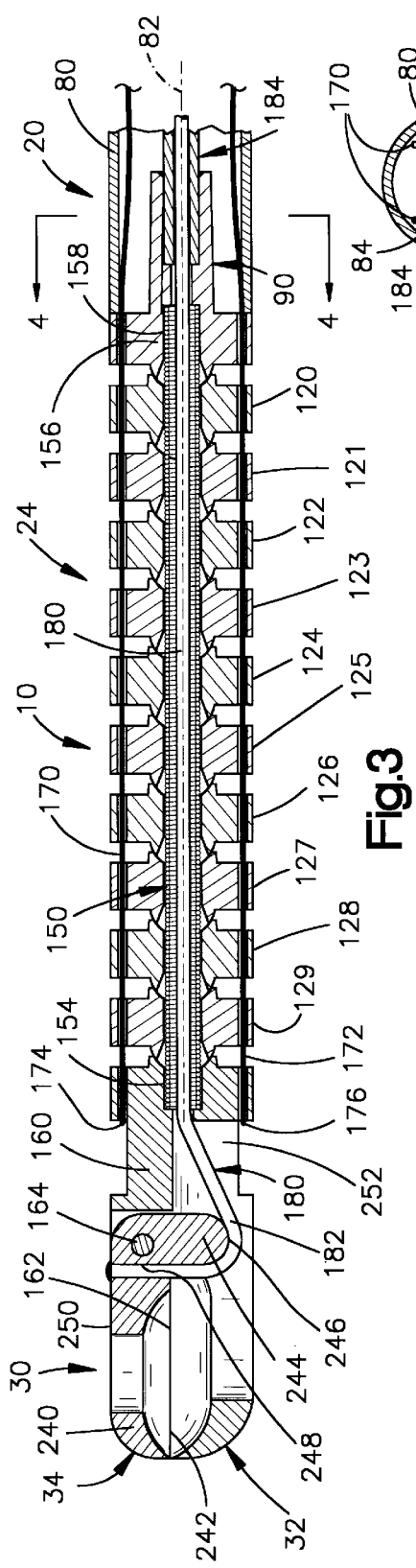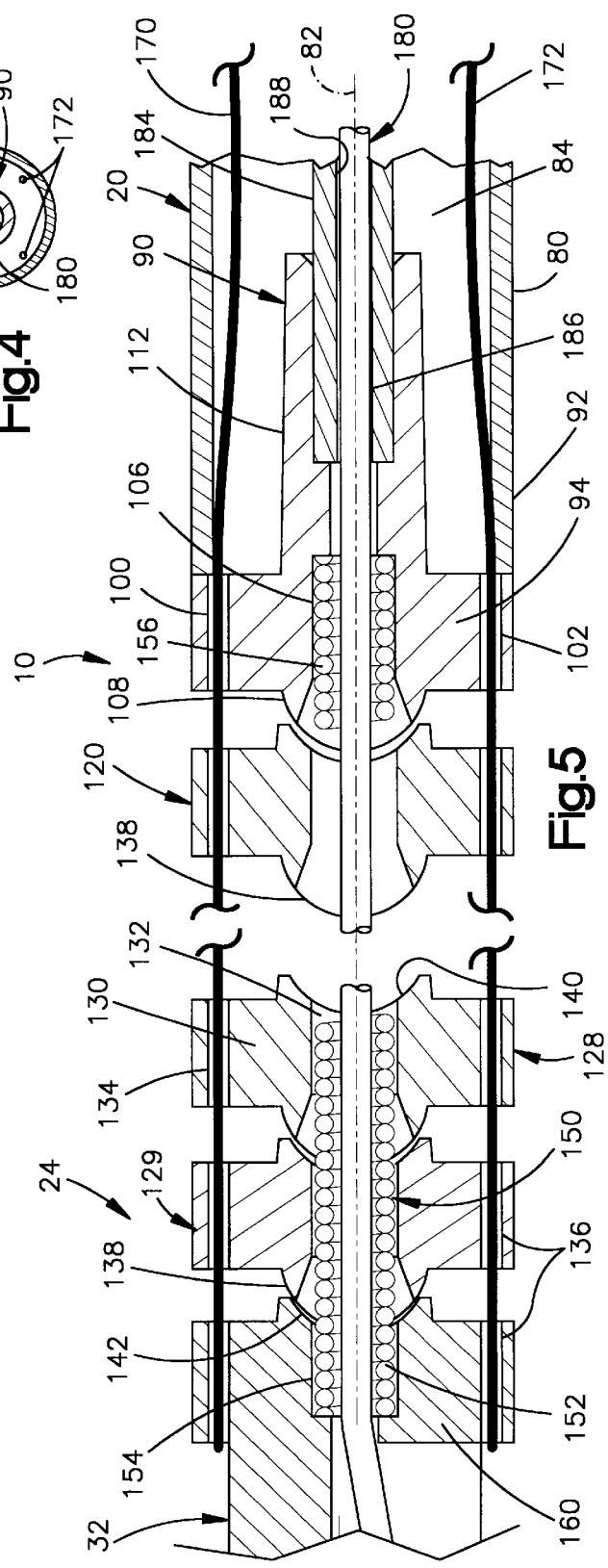

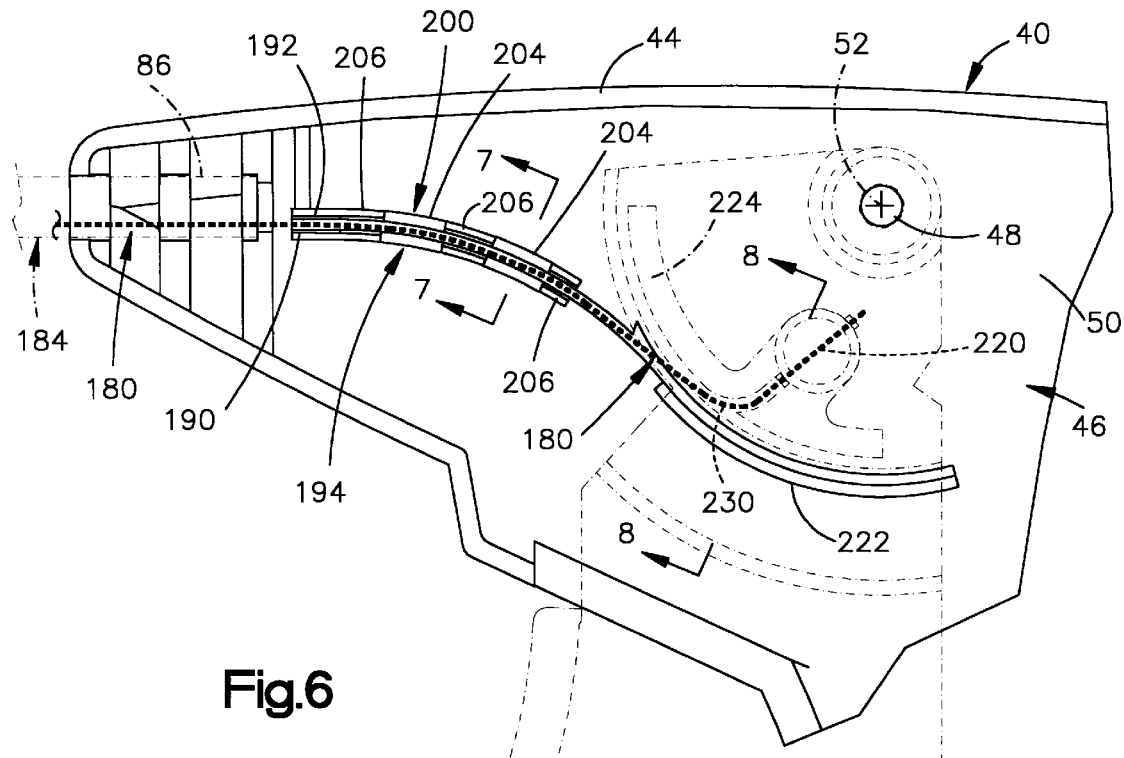
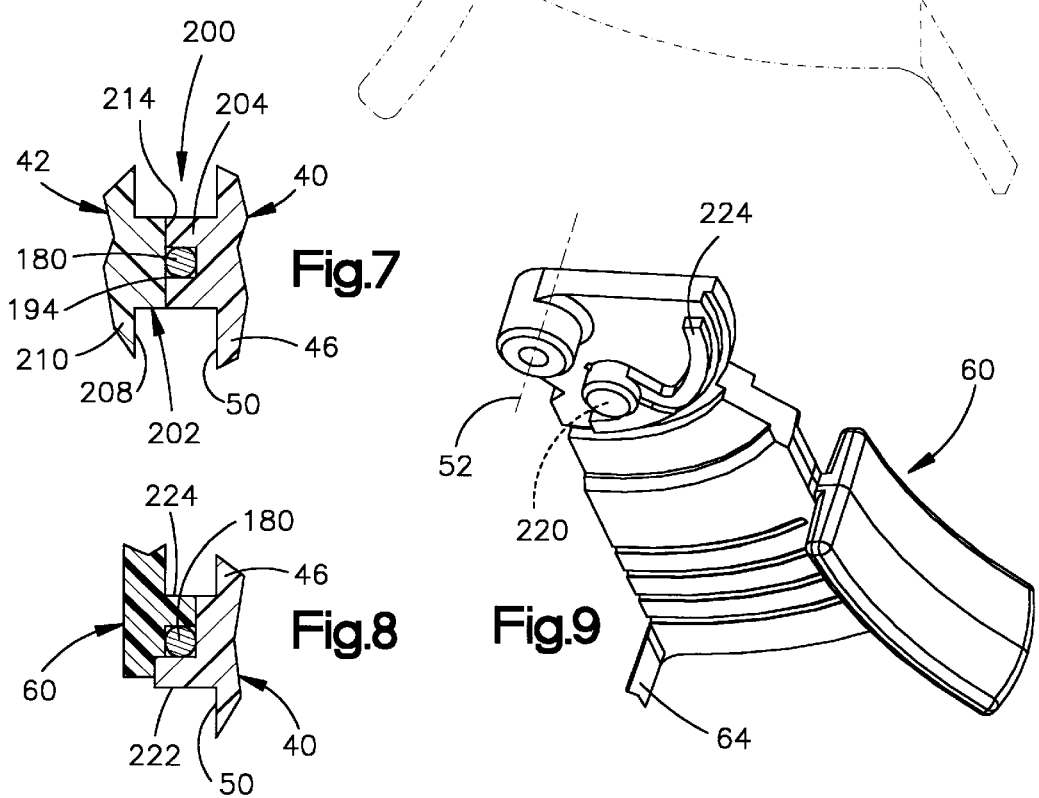
Fig.6
Fig.7
Fig.8
Fig.9

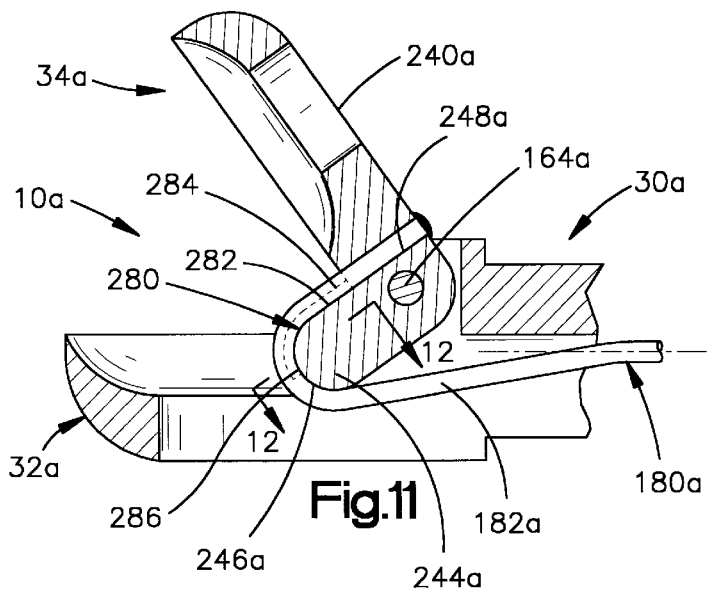
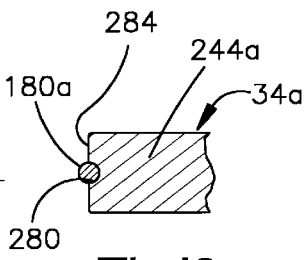
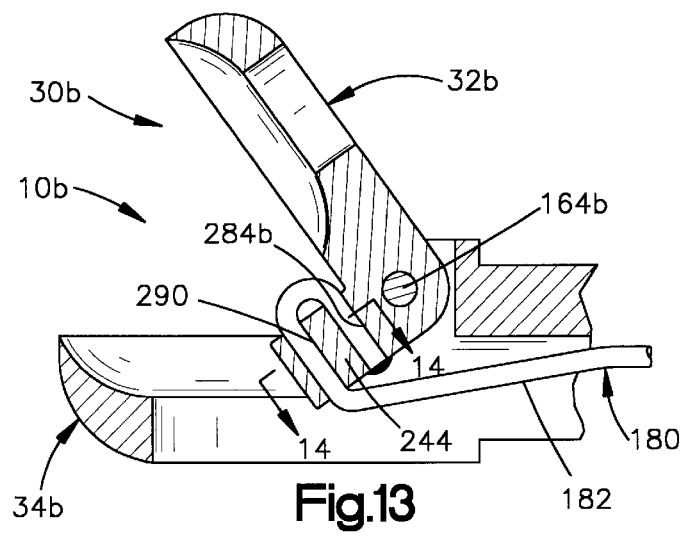
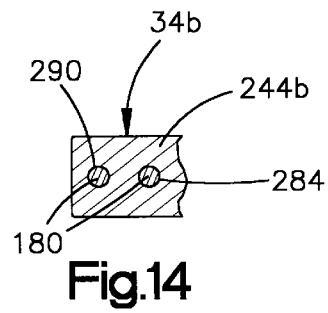
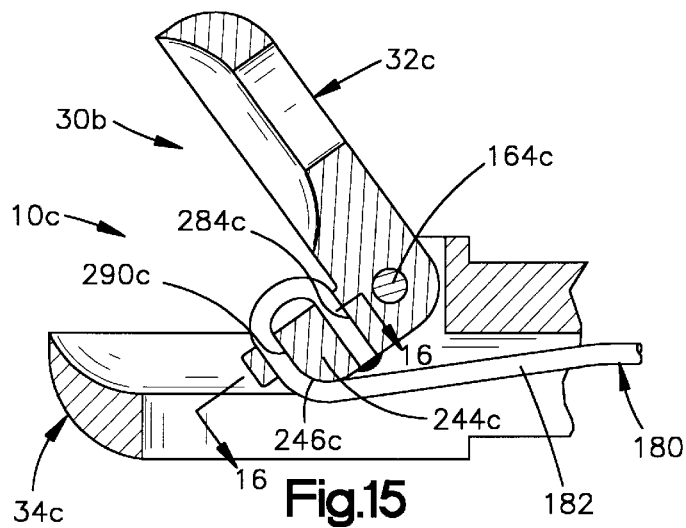
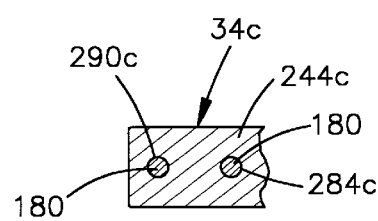

SURGICAL INSTRUMENT

BACKGROUND OF THE INVENTION

The present invention relates to a surgical instrument and, more particularly, to an endoscopic surgical instrument which may be used for cutting and/or removal of tissue.

SUMMARY OF THE INVENTION

The present invention is a surgical instrument including a handle, a rigid stem section extending from the handle, and a flexible stem section extending from the rigid stem section. A surgical tool connected with a distal end of the flexible stem section includes a fixed part fixed for movement with the distal end of the flexible stem section and a movable part supported on the fixed part for pivotal movement relative to the fixed part about a pivot axis. The instrument includes a flexible actuator cable having a first end portion movable by an actuator member on the handle, an intermediate portion extending through the flexible stem section, and a second end portion extending through a passage in the movable part and soldered in the passage. The flexible actuator cable transmits force from the actuator member to the movable part to effect pivotal movement of the movable part about the pivot axis.

BRIEF DESCRIPTION OF THE DRAWINGS

Further features of the present invention will become apparent to those skilled in the art to which the present invention relates from reading the following specification with reference to the accompanying drawings, in which:

FIG. 1 is a side elevational view, with parts removed, of a surgical instrument constructed in accordance with a first embodiment of the present invention;

FIG. 2 is an enlarged view of a flexible stem section of the surgical instrument of FIG. 1, shown in a bent condition;

FIG. 3 is an enlarged sectional view of the flexible stem section, shown in a linear condition;

FIG. 4 is a view taken along line 4—4 of FIG. 3;

FIG. 5 is a further enlarged view of portions of FIG. 3;

FIG. 6 is a fragmentary elevational view of the surgical instrument with parts removed;

FIG. 7 is a sectional view taken generally along line 7—7 of FIG. 6;

FIG. 8 is a sectional view taken generally along line 8—8 of FIG. 6;

FIG. 9 is a perspective view of a trigger which forms part of the surgical instrument;

FIG. 11 is an enlarged view of a portion of a surgical instrument constructed in accordance with a second embodiment of the present invention;

FIG. 12 is a fragmentary sectional view taken generally along line 12—12 of FIG. 11;

FIG. 13 is an enlarged view of a portion of a surgical instrument constructed in accordance with a third embodiment of the present invention;

FIG. 14 is a fragmentary sectional view taken generally along line 14—14 of FIG. 13;

FIG. 15 is an enlarged view of a portion of a surgical instrument constructed in accordance with a fourth embodiment of the present invention; and FIG. 16 is a fragmentary sectional view taken generally along line 16—16 of FIG. 15.

DESCRIPTION OF PREFERRED EMBODIMENTS OF THE INVENTION

Figure 10:
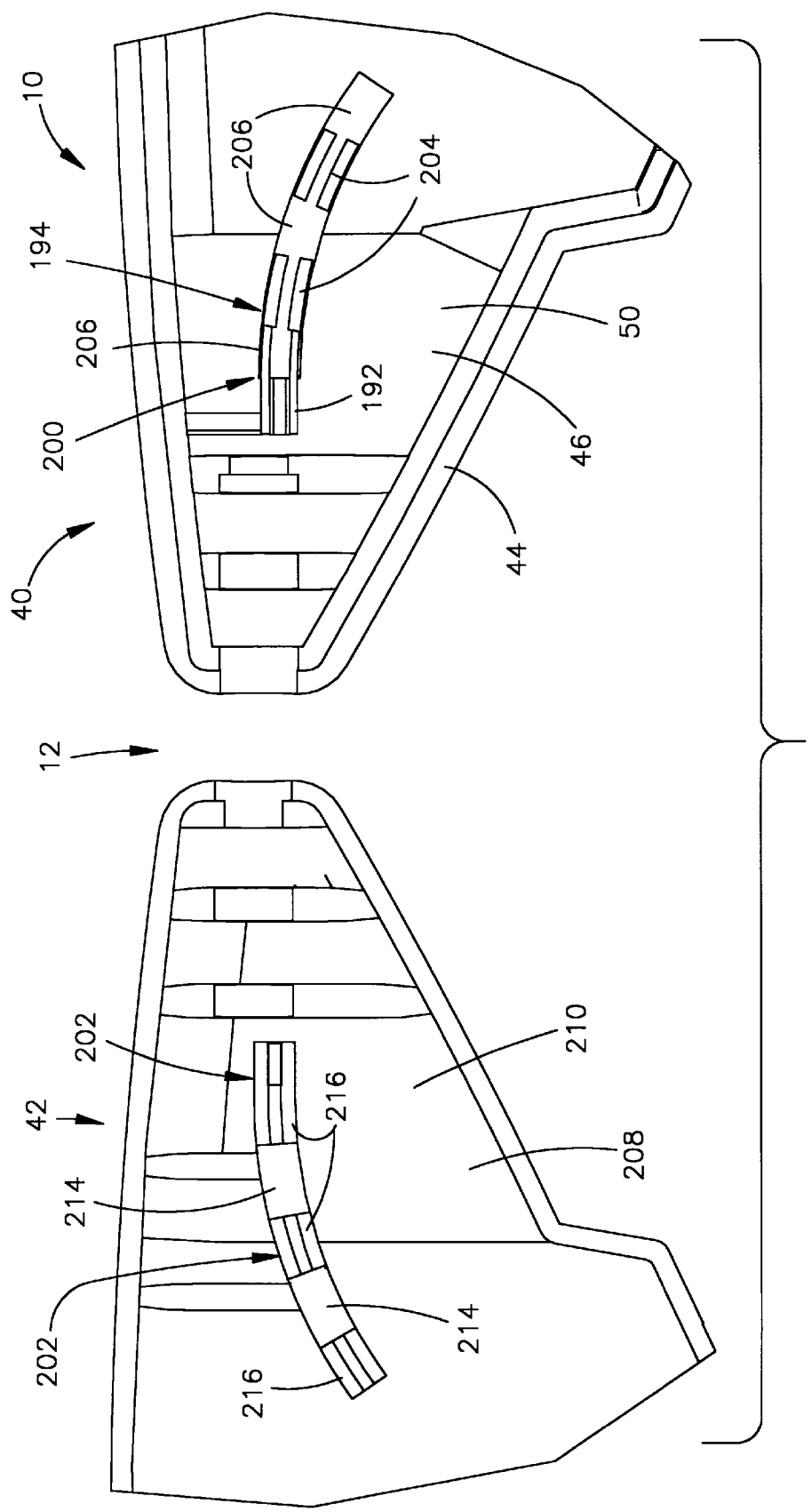
FIG. 10 is a schematic view of the two parts of the handle of the surgical instrument, shown in a separated condition.

The present invention relates to a surgical instrument and in particular to an endoscopic surgical instrument which may be used for cutting and/or removal of tissue. The present invention is applicable to various surgical instrument constructions. As representative of the present invention, FIG. 1 illustrates a surgical instrument 10.

The surgical instrument 10 includes generally a handle 12 with an actuator assembly 14 and a deflection control assembly 16. A proximal end portion 18 of a first stem section or rigid stem section 20 is fixed to the handle 12. A proximal end portion 22 of a second stem section or flexible stem section 24 is connected with a distal end portion 26 of the rigid stem section 20. A surgical tool 30, including a fixed tool part 32 (FIG. 2) and a movable tool part 34, is located on a distal end portion or tip portion 36 of the flexible stem section 24.

The handle 12 (FIGS. 1 and 10) of the surgical instrument 10 has a pistol grip configuration which is configured to be manually gripped by a person's hand. The handle 12 includes a first handle part 40 and a second handle part 42 which in overall configuration are substantially mirror images of each other and which are joined together to form the handle. The second handle part 42, overlies the first handle part 40 and covers the other parts of the surgical instrument 10 which are mounted on the first handle part. The second handle part 42 is, for clarity, shown only fragmentarily (FIG. 1).

The first handle part 40 has an outer peripheral rim 44 extending around a main wall 46. A trigger pivot pin 48 projects from the inner side surface 50 of the main wall 46 of the first handle part 40. The trigger pivot pin 48 defines a trigger pivot axis 52. A deflection control lever pivot pin 54 projects from the inner side surface 50 of the main wall 46 of the first handle part 40, at a location spaced apart from the trigger pivot pin 48.

The actuator assembly 14 includes a trigger 60. The trigger 60 is supported on the trigger pivot pin 48 for pivotal movement relative to the handle 12 about the pivot axis 52. The trigger 60 extends out of the handle 12 and is manually engageable to effect pivotal movement of the trigger relative to the handle. A generally V-shaped spring 64 formed as one piece with the trigger 60 engages a spring support pin 66 on the first handle part 40. The spring 64 biases the trigger 60 to an unactuated position, as shown in FIG. 1, relative to the handle 12.

The deflection control assembly 16 includes a deflection control lever 70. The deflection control lever 70 is supported on the deflection control lever pivot pin 54 for pivotal movement relative to the handle 12. A manually engageable portion 72 of the deflection control lever 70 projects from the handle 12. A tensioner 74 is disposed between the deflection control lever 70 and the first handle part 12. The tensioner 74 is supported for limited rotation about the pivot pin 54.

It should be understood that the deflection control assembly 16 is illustrated only schematically. Other types of deflection control assemblies can be substituted. Thus, the deflection control assembly 16 is illustrative of the various types of deflection control assemblies which can be used to provide the force for bending the flexible stem section 24 of the surgical instrument 10 in the manner illustrated.

The rigid stem section 20 of the surgical instrument 10 includes a rigid main tube 80 which extends between and interconnects the handle 12 and the flexible stem section 24. The main tube 80 may be made from a suitable metal or plastic, as desired. The main tube 80 has a longitudinal central axis 82 (FIGS. 3 and 5) which forms a longitudinal central axis of the surgical instrument 10. A central passage 84 extends axially along the length of the main tube 80. A proximal end portion 86 (FIG. 1) of the main tube 80 is fixed to the handle 12.

The rigid stem section 20 includes an interface element 90 (FIG. 5) fixed to a distal end portion 92 of the main tube 80. The interface element 90 has a disc-shaped main body portion 94. Upper and lower pairs of deflection control wire passages 100 and 102 (only one of each pair is shown) extend axially through a radially outer section of the main body portion 94 of the interface element 90.

A spring pocket 106 is formed in the main body portion 94 of the interface element 90. The spring pocket 106 has a cylindrical configuration centered on the axis 82. The spring pocket 106 faces distally, that is, in a direction away form the handle 12.

A rib 108 is located on the distal end face 110 of the main body portion 94 of the interface element 90. The rib 108 is located between the two pairs of control wire passages 100 and 102. The rib 108 has a convex, semi-cylindrical cross sectional configuration extending into and out of the plane of the paper as viewed in FIG. 3. The semi-cylindrical configuration of the rib 108 provides for bending or pivotal movement of the flexible stem section 24 relative to the rigid stem section 20, only in an upward or downward direction as viewed in FIG. 1–3.

A hollow tubular stem portion 112 of the interface element 90 extends proximally from the main body portion 94 of the interface element. The stem portion 112 of the interface element 90 extends inside the central passage 84 in the main tube 80.

The flexible stem section 24 of the surgical instrument 10 includes a plurality of relatively pivotable vertebrae or links 120–129 arranged between the interface element 90 and the surgical tool 30. In the illustrated embodiment, ten identical vertebrae 120–129 are provided. The number of vertebrae can differ, depending on the desired length and amount of bending movement of the flexible stem section 24.

Each one of the vertebrae 120–129 has an annular, disc-shaped main body portion 130 (FIG. 5) generally similar in configuration to the main body portion 94 of the interface element 90. A cylindrical spring passage 132, centered on the axis 82, extends axially through each one of the vertebrae 120–129. Upper and lower pairs of deflection control wire passages 134 and 136 (only one of each pair is shown) extend axially through a radially outer section of the main body portion 94 of each vertebrae 120–129.

The distal end face of each one of the links 120–129 has a convex, semi-cylindrical rib 138. The ribs 138 on the links 120–129 are identical in configuration and orientation to the rib 108 on the interface element 90. In each one of the links 120–129 the spring passage 132 extends axially through the rib 138. The spring passage 132 widens as it extends distally from the main body portion 130 through the rib 138.

The proximal end face of each one of the links 120–129 has a concave, semi-cylindrical socket 140. Each one of the sockets 140 has a concave configuration adapted to pivotally receive one of the ribs 138.

The links 120–129 are arranged relative to the rigid stem section 20 so that the socket 140 on the most proximal link 120 receives the rib 108 on the interface element 90. The rib 138 on the most proximal link 120 is received in the socket 140 on the next most proximal link 122. In a similar manner, the ribs 138 on each one of the links 122–128 are received in the sockets 140 on the links 123–129, respectfully. The rib 138 on the most distal link 129 is received in a socket 142 (FIG. 5) on the fixed part 32 of the surgical tool 30.

All the links 120–129 of the flexible stem section 24 are thus supported on the rigid stem section 20 for pivotal movement relative to the rigid stem section. The surgical tool 30 is supported on the flexible stem section 24 for pivotal movement relative to the flexible stem section and to the rigid stem section 20. The surgical tool 30, as viewed in FIGS. 1–3 and 5, is movable in the plane of the paper.

The fixed jaw 32 (FIG. 3) of the surgical tool 30 has a support portion 160 and a cutting edge 162. A proximally facing spring pocket 154 is formed in the support portion 160 of the fixed jaw 32. A pivot pin 164 is mounted in the support portion 160 of the fixed jaw 32 and defines a pivot axis for pivotal movement of the movable jaw 34 relative to the fixed jaw 32.

The flexible stem section 24 includes an extension spring 150 for transmitting axial load between the surgical tool 30 and the rigid stem section 20 of the surgical instrument 10. The extension spring 150 is made from a suitable material, preferably stainless steel. In the illustrated embodiment, the extension spring 150 is a coiled spring, specifically, a cylindrical helical spring, made from metal wire having a circular cross section. The extension spring 150 is in a free or unstressed condition when the flexible stem section 24 is in a linear condition as shown in FIG. 2. When the extension spring 150 is in a free or unstressed condition, the coils of the spring are in abutting engagement along the length of the spring, and the spring is not compressible axially.

A first end portion 152 (FIG. 5) of the extension spring 150 is located in the spring pocket 154 in the fixed jaw 32 of the surgical tool 30. The extension spring 150 extends through the respective spring passages 132 in the stacked vertebrae 120–129, along the entire length of the flexible stem section 24. A second end portion 156 of the extension spring 150 is located in the spring pocket 106 in the interface element 90 of the rigid stem section 20.

The surgical instrument 10 includes upper and lower deflection control wires 170 and 172 for controlling bending movement of the flexible stem section 24. Each one of the wires 170 and 172 is formed as a U-shaped loop having its ends connected to the deflection control lever 70 and its center looped around the fixed jaw 32 of the surgical tool 30. The proximal ends of the deflection control wires 170 and 172, are connected for movement with the deflection control lever 70. The deflection control wires 170 and 172 extend from the deflection control lever 70 over the tensioner 74 (FIG. 1) and into the central passage 84 in the main tube 80. The tensioner 74 maintains an appropriate amount of tension on the deflection control wires 170 and 172.

The deflection control wires 170 and 172 pass through the rigid stem section 20 into the interface element 90. The deflection control wires 170 and 172 extend through the control wire passages 100 and 102 in the interface element 90, and into the control wire passages 134 and 136 in the links 120–129 of the flexible stem section 24. Central portions 174 and 176 (FIG. 3) of the deflection control wires 170 and 172 are looped around the support portion 160 of the fixed jaw 32 of the surgical tool 30.

The surgical instrument 10 includes an actuator cable 180 for effecting pivotal movement of the movable jaw 34 relative to the fixed jaw 32. The actuator cable 180 is a flexible metal cable having a first end portion 182 (FIG. 3)

fixed to the movable jaw 34 of the surgical tool 30. The movable jaw 34 of the surgical tool 30 is supported on the pivot pin 164 for pivotal movement relative to the fixed jaw 32 about the pivot pin.

The movable jaw 34 has a generally L-shaped configuration including an elongate main body portion 240 with a cutting edge 242. The cutting edge 242 on the movable jaw 34 is engageable with the cutting edge 162 of the fixed jaw 32 upon pivotal movement of the movable jaw relative to the fixed jaw from the open position shown in FIG. 5 to the closed position shown in FIG. 3. The L-shaped configuration of the movable jaw includes a moment arm 244 which extends from the main body portion 240 of the movable jaw, in a direction away from the pivot pin 164. The moment arm 244 extends in a direction generally perpendicular to the length of the cutting edge 242. The moment arm 242 has an arcuate end face or guide surface 246 presented generally away from the pivot pin 164.

A cable end passage 248 is formed in the main body portion 240 of the movable jaw 34 of the surgical instrument 10. The cable end passage 248 extends between the side surface of the movable jaw 34 on which the cutting edge 242 is formed and an opposite, outer major side surface 250 of the movable jaw 34. The cable end passage 248 extends generally parallel to the moment arm 244 and thus at a right angle to the length of the cutting edge 242 of the movable jaw 34. The cable end passage 248 is large enough in diameter so that the first end portion 182 of the actuator cable 180 can be inserted into the cable end passage. The first end portion 182 of the actuator cable 180 is soldered to the movable jaw 34 in the cable end passage 248.

The actuator cable 180 extends from the cable end passage 248 along the outside of the moment arm 244, in a direction generally away from the pivot pin 164. The actuator cable 180 then wraps around the arcuate guide surface 246 of the moment arm 244 and extends tangentially from the guide surface. The actuator cable 180 extends for a short distance through an open portion 252 of the fixed jaw 32 and into the first end portion 154 of the extension spring 150.

The actuator cable 180 extends for the entire length of the extension spring 150 and then into the stem portion 112 of the interface element 90. The dimensions of the extension spring 150 and the actuator cable 180 are selected so that the actuator cable is freely slidable axially within the extension spring but is constrained from radial movement within the extension spring. (The inner diameter of the extension spring 150 is exaggerated for clarity, in some of the drawings.)

An actuator cable guide tube 184 is received in a recess 186 in the proximal end of the stem portion 112 of the interface element 90. The actuator cable guide tube 184 has a hollow, tubular configuration centered on the axis 82 and defining a cable passage 188. The actuator cable 180 extends from the extension spring 150 of the interface element 90 into the actuator cable guide tube 184. The inner diameter of the guide tube 184 is selected so that the actuator cable 180 is freely slidable axially within the passage 188 in the guide tube but is constrained from radial movement within the guide tube.

A proximal end portion 190 (FIG. 6) of the actuator cable guide tube 184, disposed in the proximal end portion 86 of the main tube 80, is received in a linear end portion 192 of a cable guide channel 194 in the handle 12. The cable guide channel 194 is formed between opposing, complementary channel walls 200 and 202 on the first handle part 40 and the second handle part 42, respectively.

The channel wall 200 (FIG. 6) on the first handle part 40, is formed on the inner side 50 surface of the main wall 46 of the first handle part. The channel wall 200 has a castellated configuration including alternating projections 204 and recesses 206. The projections 204 of the channel wall 200 have a U-shaped cross-sectional configuration, as seen in FIG. 7, for receiving the actuator cable 180.

The channel wall 202 on the second handle part 42 is formed on an inner side surface 208 (FIG. 10) of a main wall 210 of the second handle part. The channel wall 202 has a castellated configuration including alternating projections 216 and recesses 214. The projections 216 of the channel wall 202 have a U-shaped cross-sectional configuration identical to the configuration of the projections 204 of the channel wall 200 on the first handle part 40.

The two handle parts 40 and 42 are interengaged so that the projections 204 of the channel wall 202 on the second handle part engage in the recesses 214 in the channel wall 200 on the first handle part. Also, the projections 216 of the channel wall 200 on the first handle part 40 engage in the recesses 206 in the channel wall 202 on the second handle part 42. The cable guide channel 194 (FIG. 7) which is thus defined between the first handle part 40 and the second handle part 42 has a square cross-sectional configuration. The actuator cable 180 extends from the guide tube 184 through the cable guide channel 194. The actuator cable 180 is freely slidable axially within the guide channel 194 but is constrained from radial movement within the guide channel by the channel walls 200 and 202.

The actuator cable 180 extends out of the guide channel 194 and passes between complementary, interengaging guide ribs 222 and 224 on the first handle part 40 and the trigger 60, respectively. The cable guide rib 222 on the first handle part 40 extends from the channel wall 200 along the inner side surface 50 of the main wall 46 of the first handle part. The guide rib 222 has an L-shaped cross-sectional configuration, as seen in FIG. 8. The guide rib 222 has an arcuate configuration centered on the pivot axis 52 (FIG. 6) of the trigger 60.

The guide rib 224 on the trigger 60 also has an arcuate configuration centered on the trigger pivot axis 52. The radius of curvature of the guide rib 224 on the trigger 60 is slightly less than the radius of curvature of the guide rib 222 on the first handle part 42. Thus, the guide rib 224 on the trigger 60 is closer to the trigger pivot axis 52 than is the guide rib 222 on the first handle part 42.

A second end portion 230 of the actuator cable 180 extends from the guide channel 194, radially between the two guide ribs 222 and 224, to a termination point 220 on the trigger 60 where it is clamped to the trigger. The actuator cable 180 is freely slidable axially between the two guide ribs 220 and 222, even during pivotal movement of the trigger 60, but is constrained from radial movement by the two guide ribs 222 and 224.

When the trigger 60 is pulled, the actuator cable 180 is tensioned. The tensile force on the actuator cable 180 is transmitted into the movable jaw 34 and causes the movable jaw to pivot from the open position shown in FIG. 2 to the closed position shown in FIG. 3. The movable jaw 34 moves relative to the fixed jaw 32 and relative to the flexible stem section 24.

Specifically, the actuator cable 180 applies force to the moment arm 244 of the movable jaw 34, where the actuator cable wraps around the arcuate guide surface 246 of the moment arm. The line of action of the force applied by the actuator cable 180 extends between the first end portion 154 of the extension spring 150 and the arcuate guide surface 246 on the moment arm 244. The resulting lever arm, that is, the perpendicular distance from the pivot pin 164 to the line of action of the force, increases as the movable jaw 34 pivots from the open position shown in FIG. 2 to the closed position shown in FIG. 3. As a result, the closing force of the movable jaw 34 is maximized.

The actuator cable 180 extends tangentially from the arcuate guide surface 246 on the moment arm 244. Also, the radius of curvature of the arcuate guide surface 246 is relatively large, taking into account the diameter and flexibility of the actuator cable 180. As a result, stress on the actuator cable 180 is minimized at the point where the actuator cable extends off the movable arm 34. The location of the cable end passage 248 away from the line of action of the force applied by the actuator cable 180 isolates the solder joint from the point of application of maximum force to the movable jaw 34. In addition, soldering the actuator cable 180 directly to the movable jaw 34 is a simple and relatively inexpensive procedure, which is desirable in the manufacture of a disposable surgical instrument such as the instrument 10.

Because the actuator cable 180 is constrained from radial movement along substantially its entire length between the trigger 60 and the movable jaw 34, the actuator cable is capable of transmitting a substantial amount of compressive force from the trigger 60 to the movable jaw 34. That is, when the trigger 60 is moved from the actuated position (not shown) to the unactuated position shown in FIG. 1, the force of the moving trigger is transmitted through the actuator cable 180 to cause the movable jaw 34 to move from the closed position shown in FIG. 3 to the open position shown in FIG. 2. This capability can aid in opening the surgical tool 30, for example, when there is a obstruction to the movement of the movable jaw 34. This capability exists even though the actuator cable 180 is flexible, which it needs to be so that it can bend during bending movement of the flexible stem section 24.

The flexible stem section 24 of the surgical instrument 10 can be bent to a plurality of different orientations relative to the longitudinal axis 82. The rib 108 on the interface element 90 acts as a fulcrum about which the flexible stem section 24 of the surgical instrument 10 is bendable. The surgical instrument 10 bends because of tension on one or the other of the deflection control wires 170 and 172, when the deflection control lever 70 is moved.

The end portions 174 and 176 of the deflection control wires 170 and 172 (FIG. 1) are connected with the deflection control lever 70 in a manner so that pivotal movement of the control lever in a first direction relative to the handle tensions the upper wire 170 and releases tension on the lower wire 172. Pivotal movement of the control lever 70 in a second direction, opposite to the first direction, releases tension on the upper wire 170 but tensions the lower wire 172.

For example, movement of the manually engageable portion of the deflection control lever 70 in a downward direction as viewed in FIG. 1 results in tensioning of the upper deflection control wire 170 and release of tension on the lower control wire 172. The flexible stem section 24 of the instrument 10 bends upward, as shown in FIG. 2.

Conversely, movement of the manually engageable portion of the deflection control lever 70 in an upward direction (not shown) as viewed in FIG. 1 results in tensioning of the lower deflection control wire 172 and release of tension on the upper control wire 170. The flexible stem section 24 of the instrument 10 bends downward.

The amount of bending of the flexible stem section 24 of the surgical instrument 10 is controlled by the amount of tension on the deflection control wires 170 and 172. This is controlled by the amount of movement of the deflection control lever 70 relative to the handle 12. It should be understood that the present invention is not limited to bending movement of, for example, 90° or more. Thus, the flexible stem section 24 might be independently bendable at, say, 18° at each of ten different locations along its length, thus providing a total of 180° of bending movement.

The surgical instrument 10 may be used in association with a cannula or other tubular member (not shown) which is used, in a known manner, to provide an open path through body tissue to an operating site. Once the cannula is properly positioned, the surgical instrument 10 is inserted axially through the cannula until at least the surgical tool 30 protrudes from the distal end of the cannula. A predetermined amount of the flexible stem section 24 of the surgical instrument 10 may also protrude from the distal end of the cannula. When the surgical instrument 10 is thus inserted through the cannula, and the deflection control lever 70 is moved, the flexible stem section 24 of the surgical instrument is bendable at about the location of the distal end of the cannula, to position the surgical tool 30 in the desired location. The distal end of the cannula acts as a fulcrum about which the flexible stem section 24 of the surgical instrument 10 bends. Depending on how much of the surgical instrument 10 protrudes from the distal end of the cannula, the surgical instrument bends through different arcuate paths of different lengths, at different locations along the length of the movable stem section 24.

The force transmitted by the actuator cable 180 places an axial load on the fixed jaw 32 of the surgical tool 30. The fixed jaw 32, and thus the surgical tool 30 as a whole, is urged in a direction toward the rigid stem section 20. This pulling force on the surgical tool 30 is transmitted through the fixed jaw 32 to the first end portion 152 of the extension spring 150. The length of the extension spring 150 is selected so that the extension spring carries substantially all axial load between the surgical tool 30 and the rigid stem section 20.

FIGS. 11 and 12 illustrate a portion of a surgical instrument 1a which is constructed in accordance with a second embodiment of the present invention. The surgical instrument 10a is generally similar in construction and operation to the surgical instrument 10. Parts of the surgical instrument 1a which are the same as or similar to corresponding parts of the surgical instrument 10 are given the same reference numerals with the suffix "a" attached for clarity.

In the surgical instrument 10a, a groove 280 is formed along two sides of the moment arm 244a so that the actuator cable 180a is at least partially enclosed. A first portion 282 of the groove 280 extends along the linear side 284 of the moment arm 244a extending between the cable end passage 248a and the arcuate guide surface 246a of the moment arm. A second portion 286 of the groove 280 extends along a part of the arcuate guide surface 246a of the moment arm 244a. The first end portion 182a of the actuator cable 180a is soldered to the movable jaw 34a along the length of the groove portions 282 and 286. This increased solder area can strengthen the connection between the actuator cable 180a and the movable jaw 34a. This stronger connection can enable more effective transmission of compressive force through the actuator cable 180a to move the movable jaw 34a from a closed condition (not shown) to the open condition shown in FIG. 11.

FIGS. 13 and 14 illustrate a portion of a surgical instrument 10b which is constructed in accordance with a third embodiment of the present invention. The surgical instrument 10b is generally similar in construction and operation to the surgical instrument 10. Parts of the surgical instrument 10b which are the same as or similar to corresponding parts of the surgical instrument 10 are given the same reference numerals with the suffix "b" attached for clarity.

In the surgical instrument 10b, the cable end passage 284b is formed in the moment arm 244b of the movable jaw 34b. A second cable passage 290 is formed in the movable jaw 34b, also in the moment arm 244b. The second cable passage 290 extends parallel to the cable end passage 248b, at a location spaced outwardly from the cable end passage relative to the pivot pin 164a. The actuator cable 180b extends directly from the second cable passage 290 in the moment arm 244b of the movable jaw 34b to the extension spring 150b (not shown in FIG. 13).

The actuator cable 180b is soldered in both passages 290b and 248b. This can provide increased strength for the connection between the actuator cable 180b and the movable jaw 34b, as compared to the cable connections illustrated with respect to the instruments 10 and 10a. This can, however, increase the stress on the actuator cable 180b at the location where the actuator cable exits the movable jaw 34b, when the jaw is in an open position such as shown in FIG. 13.

FIGS. 15 and 16 illustrate a portion of a surgical instrument 10c which is constructed in accordance with a fourth embodiment of the present invention. The surgical instrument 10c is generally similar in construction and operation to the surgical instrument 10b. Parts of the surgical instrument 10c which are the same as or similar to corresponding parts of the surgical instrument 10 are given the same reference numerals with the suffix "c" for clarity.

In the surgical instrument 10c, the second cable passage 290c is shorter than the second cable passage 290 (FIG. 13). The actuator cable 180c extends tangentially from an arcuate guide surface 246c on the moment arm 244c of the movable jaw 34c, at the location where the actuator cable exits the second cable passage. This design reduces the stress on the actuator cable 180c at the location where the actuator cable exits the movable jaw 34c.

From the above description of the invention, those skilled in the art will perceive improvements, changes and modifications in the invention. For example, the surgical tool 30 can have a different configuration and function so long as it has a movable part and a fixed part. Such improvements, changes and modifications within the skill of the art are intended to be covered by the appended claims.

Having described the invention, we claim:

1. A disposable surgical instrument comprising:
   a handle;
   a rigid stem section extending from said handle and defining a longitudinal axis of said surgical instrument;
   a flexible stem section extending from a distal end of said rigid stem section;
   a surgical tool connected with a distal end of said flexible stem section, said surgical tool including a fixed part fixed for movement with said distal end of said flexible stem section, said surgical tool including a movable part supported for pivotal movement relative to said fixed part about a pivot axis; and
   a flexible actuator cable having a first end portion movable by an actuator member on said handle, an intermediate portion extending through said flexible stem section, and a second end portion extending through a passage in said movable part and soldered in said passage;
   said flexible actuator cable transmitting force from said actuator member to said movable part to effect pivotal movement of said movable part about said pivot axis.

2. A surgical instrument as set forth in claim 1 wherein said movable part has a main body portion engageable with said fixed part and has a moment arm fixed to and movable with said main body portion, said moment arm extending generally perpendicular to said main body portion, said second end portion of said actuator cable being connected with said moment arm and transmitting force from said actuator member to said moment arm to effect pivotal movement of said movable part about said pivot axis.

3. A surgical instrument as set forth in claim 2 wherein said movable part has a cutting edge extending in a direction away from said pivot axis, said moment arm extending generally perpendicular to said cutting edge of said movable part, said cable end passage being located in said main body portion of said movable part.

4. A surgical instrument as set forth in claim 2 wherein said movable part has a cutting edge extending in a direction away from said pivot axis, said moment arm extending generally perpendicular to said cutting edge of said movable part, said cable end passage being located in said moment arm of said movable part.

5. A surgical instrument as set forth in claim 1 wherein said second end portion of said actuator cable extends around a curved surface on said moment arm of said movable part and extends tangentially from said curved surface to said flexible stem section.

6. A surgical instrument as set forth in claim 5 wherein said cable end passage is spaced apart from said curved surface of said moment arm of said movable part.

7. A surgical instrument as set forth in claim 5 wherein said second end portion of said actuator cable is at least partially enclosed along said curved surface of said moment arm of said movable part.

8. A surgical instrument as set forth in claim 1 wherein said movable part includes a moment arm fixed for movement with said movable part and which produces a lever arm which increases as said movable part pivots from the open position to the closed position.

9. A surgical instrument as set forth in claim 8 wherein said cable end passage is located in said moment arm of said movable part between a curved surface on said movable part and the pivot axis of said movable part.

10. A surgical instrument as set forth in claim 1 wherein said second end portion of said actuator cable extends through and is soldered in a second passage in said movable part.

11. A disposable surgical instrument comprising:
    a handle;
    a rigid stem section extending from said handle and defining a longitudinal axis of said surgical instrument;
    a flexible stem section extending from a distal end of said rigid stem section;
    a surgical tool connected with a distal end of said flexible stem section, said surgical tool including a fixed part fixed for movement with said distal end of said flexible stem section, said surgical tool including a movable part supported for pivotal movement relative to said fixed part about a pivot axis; and
    said movable part of said surgical tool having a main body portion engageable with said fixed part and having a moment arm fixed to and movable with said main body portion, said moment arm extending generally perpendicular to said main body portion;

a flexible actuator cable having a first end portion movable by an actuator member on said handle, an intermediate portion extending through said flexible stem section, and a second end portion extending around a curved surface on said moment arm and connected with said movable part;

said actuator cable transmitting force from said actuator member to said moment arm of said movable part along a line of action extending between said curved surface on said moment arm and said flexible stem section to effect pivotal movement of said movable part about said pivot axis;

said actuator cable extending tangentially from said curved surface on said moment arm, and said actuator cable applying force to said moment arm of said movable part where said actuator cable extends around said curved surface on said moment arm, whereby the perpendicular distance from said pivot axis to the line of action of the force applied by said actuator cable increases as said movable part pivots from an open position to a closed position relative to said fixed part.

12. A surgical instrument as set forth in claim 11, wherein said second end portion of said actuator cable is at least partially enclosed along said curved surface.

13. A surgical instrument as set forth in claim 11 wherein said second end portion of said actuator cable extends through a second passage in said moment arm.

* * * * *